United States Patent [19]
House

[11] 3,979,431
[45] Sept. 7, 1976

[54] PROCESS FOR PREPARING NITROAROMATIC NITRILES

[75] Inventor: Ralph House, El Sobrante, Calif.

[73] Assignee: Chevron Research Company, San Francisco, Calif.

[22] Filed: Sept. 17, 1975

[21] Appl. No.: 614,278

[52] U.S. Cl. ........................ 260/465 R; 260/251 R; 260/283 CN; 260/294.9; 260/319.1; 260/326.62; 260/329 R; 260/465 D; 260/465 G
[51] Int. Cl.² ................ C07C 121/52; C07C 121/60
[58] Field of Search ........ 260/465 R, 465 G, 465 D, 260/251 R, 283 CN, 319.1, 326.62, 329 R, 294.9

[56] References Cited
OTHER PUBLICATIONS

J. P. Wilbaut et al: Chemical Abstracts, vol. 52, pp. 15468–15469 (1958).

*Primary Examiner*—Lewis Gotts
*Assistant Examiner*—Dolph H. Torrence
*Attorney, Agent, or Firm*—G. F. Magdeburger; John Stoner, Jr.; W. Keith Turner

[57] ABSTRACT

A process for preparing nitroaromatic nitriles which comprises reacting an aromatic carbocyclic nitrile with a mixture of nitric acid and sulfuric acid at a temperature of at least 35°C and an acids-to-nitrile mol ratio of at least 3.5:1 and a nitric acid-to-nitrile mol ratio of at least 1:1.

4 Claims, No Drawings

PROCESS FOR PREPARING NITROAROMATIC NITRILES

BACKGROUND OF THE INVENTION

The present invention relates to a process for preparing nitroaromatic nitriles by the nitration of aromatic carbocyclic nitriles with a mixture comprising nitric acid and sulfuric acid at a temperature of at least 35°C, preferably as high as 40°C, and an acids-to-nitrile mol ratio of at least 3.5:1.

The use of nitric acid and mixtures of nitric acid and sulfuric acid to nitrate aromatic carbocyclic nitriles heretofore has been difficult or impossible to accomplish because the nitrating acids tend to hydrolyze the nitrile moiety. Various suggestions have been offered to overcome the hydrolization problem. The usual solution has been to refrigerate the reaction vessel so as to maintain a reaction temperature below about 0°C. As early as 1928, Baker et al., J. Chem. Soc. 1928, 426, reported that nitric acid could be utilized to nitrate benzonitrile at quantitative yields at 0°C. Since that time, attempts have been made to effect nitration of aromatic carbocyclic nitriles without the need to employ costly equipment and inefficient methods of synthesis.

U.S. Pat. No. 3,162,675, granted Dec. 22, 1964, discloses the use of nitronium salts as high-temperature nitrating agents. Nitronium fluoroborate, $NO_2BF_4$, is specifically suggested as a convenient and available nitrating agent.

Hammond et al., J. Amer. Chem. Soc. 81, 1959, pp. 1184–7, describe the use of perchloric acid and nitric cid mixtures as nitrating agents which may be employed at temperatures as high as 43°C.

Hetherington and Robinson, Chem. Soc. J. (London), 1954. Pt. 3, pp. 3512–14, describe the use of nitryl fluoride as a nitrating agent which may be employed with aromatic substrates.

Olah et al, Chem. Soc. J. (London), 1956, Pt. 4, pp. 4257–8, describe the use of nitronium tetrafluoroborate and other nitronium salts to effect nitration of aromatics at temperatures as high as 130°C.

SUMMARY OF THE INVENTION

It has been found that aromatic carbocyclic nitriles can be nitrated using a nitric acid and sulfuric acid mixture at temperatures above 35°C, preferably as high as 40°C, where the acids-to-nitrile molar ratio is from about 3.5:1 to about 4.5:1 and the nitric acid-to-nitrile mol ratio is at least 1:1, preferably 1.1:1.

DETAILED DESCRIPTION OF THE INVENTION

The process of this invention involves the preparation of nitroaromatic nitriles by the reaction of an aromatic carbocyclic nitrile with a nitrating agent which comprises a mixture of from about 20% to about 30%, by weight, nitric acid, and from about 70% to about 80%, by weight, sulfuric acid, at a temperature of at least 35°C and an acids-to-nitrile mol ratio of at least 3.5:1 and not more than 4.5:1.

Aromatic carbocyclic nitriles useful in the practice of the invention are well known and are readily prepared by conventional procedures. For example, U.S. Pat. No. 3,246,028, granted Apr. 12, 1966, describes the production of aromatic carbocyclic nitriles by the liquid-phase ammoxidation of methyl-substituted aromatic hydrocarbons. As used herein, the term "aromatic carbocyclic nitrile" includes nitriles such as benzonitriles, toluonitriles, naphthonitriles, and the like, as well as nitriles of nitrogen- and sulfur-containing heterocyclics having aromatic properties, such as cyanopyrroles, cyanoindoles, cyanopyrimidines, cyanopyridines, cyanoquinolines, cyanothiophenes, cyanothiazoles, and similar compounds. The nitriles may be substituted with groups unreactive to the nitration process, such as alkyl, halogen, nitro, carboxyl, and aldehyde.

The nitration reaction between the aromatic carbocyclic nitriles and the nitric and sulfuric acids mixture proceeds smoothly at temperatures above 35°C where the acids-to-nitrile mol ratio is at least 3.5:1. Temperatures as high as from about 50° to about 60°C may be employed, depending upon the nitrile being reacted; however, temperatures of from about 40° to 45°C are preferred for most reactions. In order to insure complete nitration it is, of course, necessary to employ a nitric acid-to-nitrile mol ratio of at least 1:1. An excess of nitric acid is advantageous and nitric acid-to-nitrile ratios of at least 1.1:1 are preferred.

The use of a sulfuric and nitric acids mixture as the nitrating agent is a central feature of the process of this invention. Suitable acids mixtures comprise from about 20% to about 30% nitric acid and from about 70% to about 80% sulfuric acid. Acids mixtures comprising less than 20% nitric acid have been found unacceptable as nitrating agents, and acids mixtures comprising more than about 30% nitric acid do not significantly improve the nitration process and are therefore uneconomical. The acids mixture is employed in the process at an acids-to-nitrile mol ratio of at least 3.5:1. Below a mol ratio of 3.5:1 the nitration yield is unacceptably low, and above a mol ratio of about 4.5:1 economics of product recovery are unacceptable. Thus, an acids-to-nitrile mol ratio of from 3.5:1 to about 4.5:1 is preferred.

The reaction is carried out in the fluid phase. Where the reactants are not liquid a suitable inert solvent capable of dissolving the aromatic carbocyclic nitrile is employed. For convenience in separating the nitrated product, a solvent miscible with water, such as tetramethylene sulfone, is preferred.

EXAMPLE

The following example further illustrates the practice of this invention.

Nitration of Benzonitrile 0.21 g of benzonitrile was added dropwise to 0.62 g of an acidic mixture comprising 22%, by weight, nitric acid and 78%, by weight, sulfuric acid. The reaction mixture was stirred vigorously and kept at 35°C by ice cooling for 30 minutes (15 minutes to to add nitrile to acids and 15 minutes to digest).

A total yield of 0.25 of nitrobenzonitrile (84% conversion) was recovered. The product was recovered by dilution with ice water, extracted with diethylene oxide and aqueous sodium carbonate, filtered, washed and dried.

In accordance with the above procedure, an equivalent amount of p-toluonitrile is substituted for benzonitrile and nitrotoluonitrile is obtained.

What is claimed is:

1. A process for preparing nitroaromatic nitriles which comprises reacting an aromatic carbocyclic nitrile with a nitrating agent comprising from about 20% to about 30% nitric acid and from about 70% to about 80% sulfuric acid at a temperature of at least 35°C and a nitrating agent-to-nitrile molar ratio of at least 3.5:1.

2. A process in accordance with claim 1, wherein said aromatic carbocyclic nitrile is benzonitrile.

3. A process in accordance with claim 1, wherein said temperature is at least 40°C.

4. A process for preparing nitrobenzonitrile which comprises reacting benzonitrile with a nitrating agent comprising about 22% nitric acid and 78% sulfuric acid at a temperature of about 40° and a nitrating agent-to-benzonitrile molar ratio of from about 3.5:1 to about 4.5:1.

* * * * *